United States Patent [19]

Vincent et al.

[11] Patent Number: 4,644,008
[45] Date of Patent: * Feb. 17, 1987

[54] PERHYDROINDOLE-2-CARBOXYLIC ACIDS AS ANTIHYPERTENSIVES

[75] Inventors: Michel Vincent, Bagneux; Georges Rémond, Versailles; Michel Laubie, Vaucresson, all of France

[73] Assignee: Adir, Neuilly-sur-Seine, France

[*] Notice: The portion of the term of this patent subsequent to Apr. 2, 2002 has been disclaimed.

[21] Appl. No.: 659,274

[22] Filed: Oct. 10, 1984

Related U.S. Application Data

[63] Continuation of Ser. No. 308,234, Oct. 2, 1981, Pat. No. 4,508,729, which is a continuation-in-part of Ser. No. 212,607, Dec. 3, 1980, Pat. No. 4,404,206.

[30] Foreign Application Priority Data

Dec. 7, 1979 [FR] France ................ 79 30046
Jul. 31, 1980 [FR] France ................ 80 16875
Oct. 2, 1980 [FR] France ................ 80 21095
Apr. 7, 1981 [FR] France ................ 81 06916

[51] Int. Cl.[4] ............ A61K 31/40; C07D 209/42
[52] U.S. Cl. ............................. 514/412; 548/452
[58] Field of Search .............................. 548/452

[56] References Cited

U.S. PATENT DOCUMENTS

| | | | |
|---|---|---|---|
| 3,501,497 | 3/1970 | Bell | 548/491 |
| 3,514,465 | 5/1970 | Posselt et al. | 546/328 |
| 4,046,889 | 9/1977 | Ondetti et al. | 514/210 |
| 4,105,776 | 8/1978 | Ondetti et al. | 514/423 |
| 4,251,444 | 2/1981 | Freed et al. | 260/244.4 |
| 4,256,751 | 5/1981 | Hayashi et al. | 546/147 |
| 4,303,583 | 12/1981 | Kim et al. | 260/239.3 |
| 4,344,949 | 8/1982 | Hoefle et al. | 546/147 |
| 4,350,633 | 9/1982 | Kim et al. | 548/452 |
| 4,374,829 | 2/1983 | Harris et al. | 260/112.5 R |
| 4,404,206 | 9/1983 | Vincent et al. | 548/452 |

· FOREIGN PATENT DOCUMENTS

| | | |
|---|---|---|
| 0012401 | 6/1980 | European Pat. Off. . |
| 0018549 | 11/1980 | European Pat. Off. . |
| 50800 | 6/1982 | European Pat. Off. ............ 548/492 |

OTHER PUBLICATIONS

Burger, Alfred; *Medicinal Chem.*, vol. I, pp. 75, 76, (1970).

Wollweber, et al., "Compounds Active on Blood Pressure", *Chem Abst.* 57: 16561 (f), (1962).
Wagner and Zook; *Synthetic Organic Chemistry*, pp. 662, 663, (1953).
Vincent, et al., "Stereoselective Synthesis . . . Perhydroindole . . . ", *Tetrahedron Letters*, vol. 23, pp. 1677–1680, (1982).
Patchett, et al., ". . . Angiotensin-Converting Enzyme Inhibitors", Nature, vol. 288, pp. 280–283, (1980).
The Merck Index, 9th Edition (1976), pp. 656, 657, Items 4840–4852.
Burger, Alfred; "Medicinal Chemistry", 3rd Edition, Part II, Relating to Antihypertensive Agents, pp. 1019–1055.
Burger, Alfred; "Medicinal Chemistry", 4th Edition, Part III, Relating to Antihypertensive Agents, pp. 324, 325.
Scriabine; "Pharmacology of Antihypertensive Drugs", Relating to Guanethidine, pp. 127, 196, 211; and Alprenolol, p. 223; and Pindolol, p. 237; and, Relating to Other Beta-Adrenoceptor Antagonists, pp. 350, 351.
Gross, et al.; "Journal of Pharmacology and Experimental Therapeutics" 1981, 216, (3), pp. 552–557.

Primary Examiner—Glenna M. Hendricks
Attorney, Agent, or Firm—Gordon W. Hueschen

[57] ABSTRACT

Compounds of the general formula:

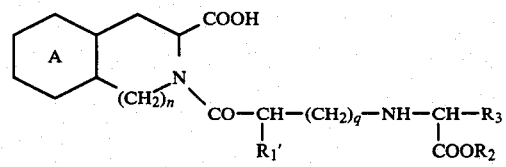

wherein:
the ring A is saturated and n=0 or 1, or
the ring A is a benzene ring and n=1,
$R_1$ represents a lower alkyl group which can carry an amino group,
$R_2$ represents a hydrogen atom or a lower alkyl group,
$R_3$ represents a straight or branched alkyl group, a mono- or di-cycloalkylalkyl or phenylalkyl group having no more than a total of 9 carbon atoms, or a substituted alkyl group, and also the salts thereof.

These compounds are useful as therapeutic drugs.

7 Claims, No Drawings

PERHYDROINDOLE-2-CARBOXYLIC ACIDS AS ANTIHYPERTENSIVES

The present application is a continuation of our prior-filed co-pending application Ser. No. 308,234, filed Oct. 2, 1981, now U.S. Pat. No. 4,508,729 issued Apr. 2, 1985, which is in turn a Continuation-in-Part of our prior-filed application Ser. No. 212,607 filed Dec. 3, 1980, now U.S. Pat. No. 4,404,206, issued Sept. 13, 1983.

The present invention relates to new substituted imino-diacids, and more particularly to substituted azabicycloalkanedicarboxylic acids, their preparation and pharmaceutical compositions which contain them.

The invention relates specifically to the compounds having the general formula

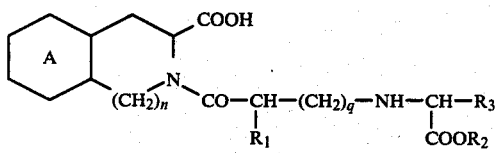

wherein:
the ring A is saturated and $n=0$ or 1, or the ring A is a benzene ring and $n=1$,
$R_1$ represents a lower alkyl group having from 1 to 4 carbon atoms which can carry an amino group,
$R_2$ represents a hydrogen atom or an alkyl group having from 1 to 4 carbon atoms,
$R_3$ represents a straight or branched alkyl group, a mono- or dicycloalkylalkyl or phenylalkyl group having no more than a total of 9 carbon atoms, or a substituted alkyl group of the formula:

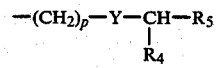

with
$R_4 = H$, a lower alkyl ($C_1$ to $C_4$) or a cycloalkyl ($C_3$ to $C_6$) group,
$R_5 = H$, a lower alkyl ($C_1$ to $C_4$), a cycloalkyl ($C_3$ to $C_6$) or an alkoxycarbonyl group,
$Y = S$ or $>N-N$ where $Q=H$, or an acetyl or benzyloxycarbonyl group, and
$p = 1$ or 2, and
$q = 0$ or 1.

The compounds of the invention contain at least one carboxy group: two in the case where $R_2=H$; and at least one salt-forming amino group: two when $Y=NH$ or $R_1=NH_2alk$. The invention thus also relates to the salts of the compounds of the general formula (I) obtained with a therapeutically compatible inorganic or organic base.

The invention also relates to the salts of addition of the compounds of formula (I) obtained with a therapeutically compatible inorganic or organic acid.

The compounds of formula (I) contain at least 3 asymmetric carbon atoms. Depending on the position of the substituents and the degree of hydrogenation, there are from 3 to 6 centres of asymmetry. The racemic compounds may be divided into their diastereoisomeric or epimeric mixtures, or resolved into their enantiomers in a known manner. The various isomers form part of the invention, as do the racemic compounds.

The invention comprises more particularly the derivatives of perhydroindole (formula I; A is saturated and $n=0$) corresponding to the general formula:

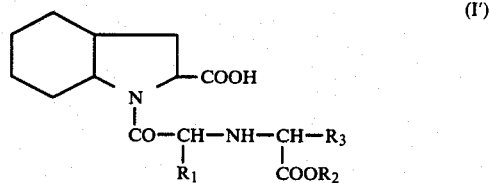

wherein the symbols $R_1$, $R_2$ and $R_3$ have the same meaning as in formula (I), in their racemic form or as optical isomers, and also the salts thereof obtained with therapeutically compatible acids or bases.

In addition, the compounds preferred are those corresponding to formula (I') in which $R_3$ is a straight or branched ($C_3$ to $C_8$)-alkyl group, a ($C_4$ to $C_8$)-cycloalkylalkyl group, or a substituted alkyl group $-CH_2-S-CHR_4R_5$ with $R_4=H$ or an alkyl group and $R_5=$ an alkoxycarbonyl group, the alkyl and alkoxy groups having from 1 to 4 carbon atoms. In addition, $R_1$ may usefully be a methyl radical.

The compounds according to the invention, and also the salts thereof, have interesting pharmacological properties. In particular, they have an inhibiting effect on certain enzymes, such as the carboxypolypeptidases, the encephalinases or kininase II. They inhibit particularly the transformation of the decapeptide angiotensin I to the octapeptide angiotensin II, which is responsible for certain cases of arterial hypertension, by acting upon the converting enzyme.

The therapeutic use of these compounds thus makes it possible to reduce or even eliminate the activity of these enzymes responsible for hypertension or cardiac insufficiency. The effect on kininase II results in an increase in the circulating bradykinin and also a reduction in the arterial pressure by this means.

The invention also relates to the pharmaceutical compositions which contain as active ingredient at least one compound of the general formula I or one of its salts of addition with an inorganic or organic acid, in conjunction with an inert, non-toxic, pharmaceutically acceptable carrier.

For therapeutic use, the compounds of the general formula I or the salts thereof are prepared in the form of pharmaceutical preparations suitable for intravenous or oral administration. In addition to the active ingredient, the pharmaceutical compositions according to the invention contain one or more inert, non-toxic carriers suitable for pharmaceutical use, and/or a binding agent, an aromatising agent, a disintegrating agent, a sweetener, a lubricant or a liquid excipient suitable for intravenous administration.

The pharmaceutical compositions according to the invention may also contain another active ingredient having a synergistic or complementary effect.

Among the latter active ingredients which may be mentioned are a diuretic and, in particular, a saliuretic, such as for example a thiazide, a dihydrothiazide, a chlorosulphamide, a dihydrobenzofuran 2-carboxylic acid or a derivative of phenoxyacetic acid. Examples of such compounds are N-(3'-chloro-4'-sulphamoylbenzamido)-2-methylindoline, ethacrynic acid and furosemide.

It is also possible to add α-adrenolytic substances such as prazosin or any other anti-hypertensive substance.

The useful posology may vary widely, depending on the age and weight of the patient, the severity of the symptoms and the method of administration. Oral administration is preferred, but intravenous administration is also perfectly suitable for the treatment of hypertension. In general terms, the unit dose will preferably range between 5 and 100 mg.

The invention includes a process for the preparation of the compounds of general formula I, which process comprises subjecting an alkyl ester of an azabicycloalkane carboxylic acid of the general formula II:

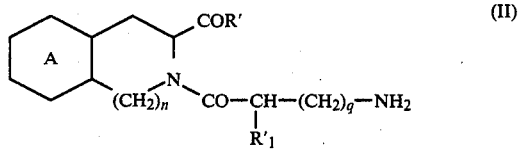

wherein the meaning of the symbols A, n and q remains the same as that mentioned previously, $R_1'$ represents a lower alkyl radical or an aminoalkyl radical in which the amino function is protected by the usual radicals, such as for example benzyloxycarbonyl or tert.-butoxycarbonyl radicals, and R' represents a lower alkoxy or hydroxy radical, to a reductive alkylation reaction by means of a compound of the general formula III:

wherein the meaning of the substituents $R_2$ and $R_3$ remains the same as that mentioned previously, in order to obtain an amine of the general formula IV:

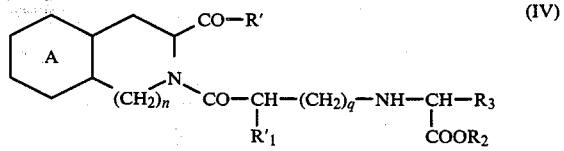

wherein R' and $R_1'$ having the meaning given previously for formula II and the symbols $R_2$, $R_3$, A, n and q retain the meanings provided before, and after reductive alkylation the intermediate compound obtained is subjected, if necessary, to the usual deprotection processes, such as for example total or partial saponification and/or hydrogenolysis, and is thus converted into a compound of formula (I).

The compounds of the general formula II are described in or may be synthesised in accordance with the European Patent Application published under No. 0031741. The above-mentioned reductive alkylation uses the process described by R. F. BORCH, M.D. BERNSTEIN, and H. DUPONT DURST, JACS 93, 2897 (1971). The process is preferably carried out in an alcoholic medium and in the presence of a neutral dehydrating agent and of an organic or inorganic cyanoborohydride. The Examples which follow illustrate the invention.

EXAMPLE 1

(3S)-2-[N-(1-carboxyethyl)-(S)-alanyl]-3-carboxy-1,2,3,4-tetrahydroisoquinoline

Step A

Laevorotatory tetrahydroisoquinoline-3-carboxylic acid.

15 g of (S)-β-phenylalanine are introduced into a three-necked flask surmounted by a condenser and then 34 ml of a 40% solution of formaldehyde, and 105 ml of concentrated hydrochloric acid are added.

The vessel is heated for 30 minutes over a boiling water-bath. A clear solution is thus obtained, the reaction medium is allowed to cool to room temperature, and then 15 ml of formaldehyde and 30 ml of concentrated hydrochloric acid are added thereto. The mixture is then heated for 3 hours under reflux, and afterwards allowed to cool. The precipitate is then separated off by filtration. After drying without heat, it is taken up in 200 ml of boiling water and 400 ml of hot ethanol. The solutions are combined and neutralised by adding a 10% ammonia solution.

Tetrahydroisoquinoline-3-carboxylic acid crystallises. The crystalline mixture is left to stand overnight in a refrigerator, and then the precipitate is separated off, filtered and washed with ethanol. 17.3 g of crude product are thus obtained. The product is dried under vacuum over phosphoric acid.

Analysis $C_{10}H_{11}NO_2 - 177$:

|  | C % | H % | N % |
| --- | --- | --- | --- |
| Calculated | 67.78 | 6.26 | 7.90 |
| Found | 66.87 | 6.20 | 7.96 |

Infra-red spectrum: $NH_2^+$ Band at 2800–2400 cm$^{-1}$; $COO^-$ Carbonyl band at 1630 cm$^{-1}$.

Rotatory power: $\alpha_D = -108°$ (c=2.2 normal NaOH).

Step B (3S)-methyl 1,2,3,4-tetrahydroisoquinoline-3-carboxylate hydrochloride.

In succession 5 g of tetrahydroisoquinoline 3-carboxylic acid and 30 ml of methanol are introduced into a three-necked flask. 6 g of thionyl chloride are added to this suspension by pouring carefully, taking care that the temperature does not exceed 0, +5°. The addition takes approximately 10 minutes. After the addition is completed, stirring is continued for 2 hours at room temperature, and then the mixture is heated to reflux for 1½ hours. Once the mixture has dissolved completely, heating is discontinued and the mixture is then evaporated to dryness. The residue is taken up three times in methanol and then evaporated to dryness. Finally, 8 g of colourless crystals are obtained and purified by trituration with ether. The crystals are separated off by filtration, washed with ether and dried. 6.4 g of methyl tetrahydroisoquinoline-3-carboxylate hydrochloride are thus obtained.

Analysis $C_{11}H_{13}NO_2ClH = 227.69$:

|  | C | H | N | Cl % |
| --- | --- | --- | --- | --- |
| Calculated | 58.03 | 6.20 | 6.15 | 15.57 |
| Found | 57.79 | 6.46 | 6.38 | 15.67 |

Infra-red spectrum Carbonyl band at 1735 cm$^{-1}$; NH$_2$+ band at 2800-2400 cm$^{-1}$.

Step C (3S)-2-[(S)-tert.butoxycarbonylalanyl]-3-methoxycarbonyl-1,2,3,4-tetrahydroisoquinoline.

6.01 g (0.0264 mol) of the hydrochloride prepared in the previous step are dissolved in 50 ml of water and the solution is rendered alkaline to pH 11 with NH$_4$OH, and then extracted with 2×50 ml of diethyl ether. The combined ether solutions are dried over calcium sulphate, filtered and evaporated to dryness. The residual amino ester (5.04 g) is dissolved in 30 ml of dimethylformamide and this solution is added to a stirred solution of 5 g (0.0264 mol) of (S)-tert.-butoxycarbonylalanine in 30 ml of dimethylformamide cooled to 0, +5° C. In succession 3.6 g (0.0264 mol) of 1-hydroxybenztriazole dissolved in 40 ml of dimethylformamide, and then 5.45 g (0.0264 mol) of dicyclohexylcarbodiimide dissolved in 30 ml of chloroform are added to the solution obtained.

The reaction mixture is stirred for 18 hours whilst being allowed to return to room temperature. The dicyclohexylurea which is formed is filtered and the filtrate, evaporated to dryness under 0.1 mm Hg, leaves a residue which is redissolved in 50 ml of ethyl acetate and filtered again to separate off a second run of dicyclohexylurea. The filtrate is washed successively with 80 ml of a saturated aqueous solution of NaCl, 2×40 ml of a 10% aqueous solution of citric acid, again with 80 ml of a saturated aqueous solution of NaCl, 2×40 ml of a saturated aqueous solution of NaHCO$_3$, and finally with a saturated aqueous solution of NaCl until neutral.

The organic phase is dried over CaSO$_4$, filtered and evaporated to dryness under vacuum. The evaporation residue is the desired product:

Weight: 9.1 g (95%); Melting point: 98°-100° (Kofler).

Analysis C$_{19}$H$_{26}$N$_2$O$_5$

|  | C | H | N % |
|---|---|---|---|
| Calculated | 62.97 | 7.23 | 7.73 |
| Found | 63.15 | 7.05 | 7.97 |

Step D (3S)-2-[(S)-tert.butoxycarbonylalanyl]-3-carboxy-1,2,3,4-tetrahydroisoquinoline.

1.45 g of (0.004 mol) of the compound prepared in the previous step are dissolved in 20 ml of methanol, and 4.4 ml (0.004 mol) of normal aqueous sodium hydroxide solution are added to the resulting solution.

The solution is left for 20 hours at room temperature. The methanol is evaporated under vacuum by water jet pump and the residue is taken up in 20 ml of water. After extraction of the unsaponified material by means of ethyl acetate, the aqueous phase is acidified with 4.4 ml of normal HCl. The precipitate which forms is extracted with 2×20 ml of ethyl acetate which is dried over CaSO$_4$, filtered and evaporated. The residue obtained is the desired product:

Weight: 1.3 g (93%)

Analysis C$_{18}$H$_{24}$N$_2$O$_5$:

|  | C | H | N % |
|---|---|---|---|
| Calculated | 62.05 | 6.94 | 8.04 |
| Found | 61.54 | 6.93 | 7.78 |

Step E (3S)-2-[(S)-alanyl]-3-carboxy-1,2,3,4-tetrahydroisoquinoline.

1.1 g (0.00316 mol) of the derivative prepared in the previous step are stirred at +5° C. with 4.5 ml of trifluoroacetic acid whilst protected from humidity.

The resulting solution is concentrated to dryness under 0.1 mm Hg. The crystalline, hygroscopic evaporation residue is the desired product, in the form of the trifluoroacetate solvated by means of 0.5 mol of trifluoroacetic acid:

Weight: 1.3 g (98%).

Analysis C$_{32}$H$_{35}$F$_9$N$_4$O$_{12}$:

|  | C % | H % | N % |
|---|---|---|---|
| Calculated | 45.83 | 4.21 | 6.68 |
| Found | 45.99 | 4.62 | 6.55 |

0.7 g (0.0019 mol) of the above trifluoroacetate are transformed into 0.45 g (94%) of the corresponding free amino acid by being passed over 50 g of sulphonated resin (Dowex 50 W×8 H+), followed by washing out with 500 ml of normal ammonia solution.

Melting point: 170° C. (decomposition).

Step F (3S)-2-[(S)-N-(1-carboxyethyl)-alanyl]-3-carboxy-1,2,3,4-tetrahydroisoquinoline.

0.849 g (0.0034 mol) of 2-[(S)-alanyl]-3-carboxy-1,2,3,4-tetrahydroisoquinoline are disoled in the presence of 1.9 g (0.0216 mol) of pyruvic acid at 25° C. in 22 ml of normal sodium hydroxide solution and 50 ml of pH 7 buffer taken from a solution prepared from 50 ml of 0.1 molar solution of monsodium phosphate and 29.1 ml of N/10 sodium hydroxide solution. 0.45 g (0.0072 mol) of sodium cyanoborohydride are added all at once. The reaction mixture is left at room temperature for 22 hours.

The excess sodium cyanoborohydride is decomposed by the addition of 6 ml of concentrated hydrochloric acid. The resulting solution is passed over an ion exchange resin (Dowex 50 H+). After washing out the resin with distilled water until there are no chlorine ions present, the product fixed on the resin is removed by washing out with 1 liter of normal aqueous ammonia solution. The ammoniacal solution is concentrated to dryness under vacuum by water jet pump. The evaporation residue is the monoammonium salt of the desired product. Weight obtained: 0.8 g (69.7%).

Analysis C$_{16}$H$_{23}$N$_3$O$_5$:

|  | C % | H % | N % |
|---|---|---|---|
| Calculated | 56.96 | 6.64 | 12.95 |
| Found | 57.79 | 6.69 | 12.70 |

EXAMPLE 2

(3S)-2-[(2RS)-3-(1-carboxyethylamino)-2-methylpropanoyl]-3-carboxy-1,2,3,4-tetrahydroisoquinoline.

Prepared as in Example 1 (Step C), starting from (2RS)-3-tert.butoxycarbonylamino-2-methylpropanoic acid and (3S)-3-methoxycarbonyl-1,2,3,4-tetrahydroisoquinoline.

The (3S)-2-[(2RS)-3-tert.butoxycarbonylamino-2-methylpropanoyl]-3-methoxycarboxyl-1,2,3,4-tetrahydroisoquinoline obtained is saponified with aqueous sodium hydroxide solution, using the method described in Example 1 (Step D).

The (3S)-2-[(2RS)-3-tert.butoxycarbonylamino-2-methylpropanoyl]-3-carboxy-1,2,3,4-tetrahydroisoquinoline obtained is treated with trifluoroacetic acid according to the method in Example 1 (Step E), providing (3S)-2-[(2RS)-3-amino-2-methylpropanoyl]-3-carboxy-1,2,3,4-tetrahydroisoquinoline trifluoroacetate, which is transformed into the hydrochloride by being dissolved in an excess of normal HCl and concentrated to dryness.

Analysis $C_{14}H_{19}Cl\ N_2O_3$:

|  | C | H | N | Cl % |
|---|---|---|---|---|
| Calculated | 56.28 | 6.41 | 9.38 | 11.87 |
| Found | 56.44 | 6.59 | 9.04 | 11.94 |
|  | 56.94 | 6.62 | 8.97 | 11.87 |

1.3 g (0.005 mol) of (3S)-2-[(2RS)-2-methyl-3-aminopropanoyl]-3-carboxy-1,2,3,4-tetrahydroisoquinoline hydrochloride obtained in the previous step are dissolved in 20 ml of methanol containing 0.009 mol of HCl and 0.515 g of 94% (0.0055 mol) pyruvic acid. The solution is hydrogenated under a pressure of 0.5 bar in the presence of 1 g of 10% palladinised charcoal. Approximately half of the theoretical amount of hydrogen is absorbed within 1 hour. The suspension is filtered, and 0.515 g of pyruvic acid are added to the filtrate. It is then neutralised with triethylamine to pH 7-7.2. After the addition of 1 g of 10% palladinised charcoal, the suspension is hydrogenated again under a pressure of 0.5 bar, until the starting primary amine has disappeared: this is checked by TLC revealing said amine by means of ninhydrin.

The reaction mixture is filtered and the concentrated filtrate is dissolved in 25 ml of water and passed over 125 ml of ion exchange resin (Dowex 50 $H^+$). The product fixed on the resin is washed out with 500 ml of normal aqueous ammonia solution, then 260 ml of distilled water. The combined washings are evaporated to dryness. The evaporation residue is the desired product in the form of the monoammonium salt.

Weight obtained: 0.6 g.
Analysis $C_{17}H_{25}NHD\ 3O_5$:

|  | C % | H % | N % |
|---|---|---|---|
| Calculated | 58.11 | 7.17 | 11.43 |
| Found | 58.91 | 6.93 | 11.96 |

EXAMPLE 3

(2S)1-{(S)-N-[(1RS)-1-carboxyethyl]-alanyl}-2-carboxyperhydroindole.

Step A (2RS)-2-carboxyinodline.

31.5 g of the above indoline (86%) are obtained by saponification in 250 ml of normal sodium hydroxide solution and 150 ml of ethanol for 8 hours at room temperature of 43 g (0.224 mol) of the corresponding ethyl ester prepared according to E. J. COREY et al. (J. Amer. Chem. Soc. 1970 92, p. 2476).

The aqueous alcoholic solution is concentrated to ½, neutralised with 25 ml of 10N hydrochloric acid, and the precipitate formed is filtered, washed with water, and dried.

The crude acid is purified by being passed through an ion exchange resin column (Dowex 50 W×8$H^+$) and washed out with 2N aqueous ammonia solution. The ammonium salt obtained is dissolved in the minimum quantity of water and the acid precipitated by the theoretical amount of HCl. It is dried, washed with water, and air-dried.

Analysis (of ammonium salt) $C_9H_{12}N_2O_2$:

|  | C % | H % | N % |
|---|---|---|---|
| Calculated | 59.99 | 6.71 | 15.54 |
| Found | 60.22 | 6.71 | 15.06 |
|  | 59.93 | 6.71 | 15.29 |

Step B (2S)-2-carboxyindoline.

60.5 g (0.37 mol) of (DL)-2-carboxyindoline prepared in Step A are added to a solution of 44.9 g (0.37 mol) of (+)-α-methylbenzylamine in 400 ml of anhydrous ethanol. The precipitate obtained is filtered and digested in 350 ml of anhydrous isopropanol under reflux. After cooling, the suspension is filtered, and the precipitate is washed with a little isopropanol and dried.

Weight of (L)-2-carboxyindoline, (+)-α-methylbenzylamine salt obtained 29.8 g.

$\alpha_D^{21} = 5.3°$ (C=1% ethanol).

The (2S)-2-carboxyindoline is prepared in a theoretical yield by dissolving 10 g of the above-mentioned salt (0.029 mol) in 50 ml of water and acidifying it with 29 ml of normal hydrochloric acid.

The precipitate is filtered washed with water, distilled, and dried. Optical purity: 96% (VPC after converting into the form of (−)-camphanic acid amide.

The (2R)-2-carboxyindoline was obtained by the same process, starting from (RS)-carboxyindoline and (−)-α-methylbenzylamine.

The absolute configurations of the (S) and (R) acids were determined as follows:

Analytical amounts (approx. 0.5 g) of each of the acids are converted into ethyl esters by treatment with thionyl chloride and ethanol according to the process described in Step C.

The esters are reduced by lithium aluminum hydride according to E. J. COREY (loc.cit.) to the corresponding primary alcohols, which are identified by their rotatory power with the alcohols described by E. J. COREY, the respective absolute configurations of which are known.

Step C (2S)-2-ethoxycarbonylperhydroindole.

11 g of (L)-2-carboxyindoline, (+)-α-methylbenzylamine salt (0.032 mol) prepared in Step B are dissolved in 100 ml of water and converted into the corresponding acid by the addition of 32 ml of N HCl. The acid is dried, washed with water and dried in a desiccator over phosphoric anhydride, then suspended in 50 ml of anhydrous ethanol. At a temperature of 0, +5°, 3.9 ml of thionyl chloride are added within 10 minutes whilst stirring, and stirring is continued for 1 hour at 25° C., then 1 hour at 50° C.

The mixture is left overnight at 25°, then concentrated to dryness under vacuum by water jet pump at 40° and taken up with 50 ml of anhydrous benzene and filtered.

The (2S)-2-ethoxycarbonylindoline hydrochloride obtained is hydrogenated in solution in 150 ml of water in the presence of 2 g of palladinised charcoal for 8 hours at 45° C. under 50 kg/cm² pressure.

After cooling and filtration of the catalyst, the filtrate is evaporated to dryness. The residue is the desired product in the form of the hydrochloride.

Weight: 6.9 g (93%).

Analysis $C_{11}H_{20}ClNO_2$:

|  | C % | H % | N % | Cl % |
|---|---|---|---|---|
| Calculated | 56.52 | 8.62 | 5.99 | 15.17 |
| Found | 55.52 | 8.53 | 5.96 | 15.16 |

Step D (2S)-N-[(S)-t-Boc.-alanyl]-2-ethoxycarbonylperhydroindole.

A solution comprising 3 g (0.0128 mol) of (2S)-2-ethoxycarbonylperhydroindole hydrochloride prepared in the previous step (C), 15 ml of dried dimethylformamide (DMF) and 1.8 ml of triethylamine is added to a solution, cooled to +5° C. and stirred, of 2.42 g (0.0128 mol) of L-t-Boc.-alanine in 15 ml of DMF. To the resulting mixture there are then added in succession a solution of 1.7 g (0.0128 mol) of N-hydroxybenztriazole in 20 ml of DMF, then a solution of 2.64 g (0.0128 mol) of dicyclohexylcarbodiimide in 15 ml of dry chloroform.

After 65 hours' stirring at 25°, the dicyclohexylurea formed is filtered and washed with ethyl acetate. The combined filtrates are washed successively with 80 ml of a saturated aqueous solution of NaCl, 2×40 ml of concentrated citric acid solution, 2×40 ml of a saturated aqueous solution of NaHCO₃, then again with 2×40 ml of NaCl solution.

The organic solution is dried over CaSO₄, filtered, concentrated to dryness under vacuum by water jet pump, and the residue is taken up in 100 ml of ethyl acetate. The solution is filtered to eliminate the last traces of dicyclohexylurea, and the filtrate which is concentrated to dryness leaves a residue which is the desired product in the form of a very viscous oil.

Weight: 3.8 g (81%).

Analysis $C_{19}H_{32}N_2O_5$:

|  | C % | H % | N % |
|---|---|---|---|
| Calculated | 61.93 | 8.75 | 7.60 |
| Found | 61.76 | 8.56 | 7.77 |

Step E (2S)-N-[(S)-t-Boc-alanyl]-2-carboxyperhydroindole.

3.6 g (0.0098 mol) of ester obtained in Step D are dissolved in 30 ml of methanol in the presence of 11 ml of normal aqueous sodium hydroxide solution.

After 20 hours at 25°, the methanol is evaporated under vacuum by water jet pump and 60 ml of water are added. The solution is washed with 2×50 ml of ethyl acetate to eliminate the unsaponified material, then acidified with 11 ml of N hydrochloric acid. The white precipitate formed is extracted with 2×50 ml of ethyl acetate, which are combined and washed with water, dried over CaSO₄, filtered and concentrated to dryness. The residue is the desired product:

Weight: 1.9 g (57%).

Analysis $C_{17}H_{28}N_2O_5$:

|  | C % | H % | N % |
|---|---|---|---|
| Calculated | 59.98 | 8.29 | 8.23 |
| Found | 59.10 | 8.16 | 7.81 |

Step F (2S)-1-[(S)-alanyl]-2-carboxyperhydroindole.

1.6 g (0.0047 mol) of acid prepared in the previous step (E) are stirred at a temperature of 0, +5° C. in solution in 10 ml of trifluoroacetic acid for 1 hour, and then for another 15 minutes at room temperature.

After being evaporated to dryness under vacuum by vane pump, the residue dissolved in 15 ml of water is passed over an ion exchange resin column (Dowex W+8H⁺). The column is washed out with 1 liter of 2N aqueous ammonia solution. The washings are concentrated to dryness under vacuum. The residue obtained is the desired product.

Weight: 0.90 g (95%).

Analysis $C_{12}H_{20}N_2O_3$:

|  | C % | H % | N % |
|---|---|---|---|
| Calculated | 59.98 | 8.39 | 11.10 |
| Found | 58.53 | 8.24 | 11.43 |

Step G (2S)-1-{(S)-N-[(1RS)-1-carboxyethyl]-alanyl}-2-carboxyperhydroindole.

0.7 g (0.00291 mol) of (2S)-N-[(S)-alanyl]-2-carboxyperhydroindole prepared in the previous step (F) and 1.67 g (0.0183 mol) of pyruvic acid are dissolved in 18 ml of normal aqueous sodium hydroxide solution and 40 ml of pH 7 buffer, and the solution obtained is subjected to reduction with 0.400 g (0.0064 mol) of sodium cyanoborohydride as described in Example 1, Step F.

After treatment with concentrated hydrochloric acid and being passed over an ion exchange resin (Dowex 50H⁺), the final ammoniacal washings, when evaporated to dryness, leave 0.76 g (79%) of residue which is the desired product in the form of monoammonium salt.

Analysis $C_{15}H_{27}N_3O_5$:

|  | C % | H % | N % |
|---|---|---|---|
| Calculated | 54.70 | 8.26 | 12.76 |
| Found | 54.10 | 7.78 | 12.77 |

EXAMPLE 4

(2S)-1-{N-[2-((1RS)-1-ethoxycarbonylethylthio)-(1RS)-1-ethoxycarbonylethyl]-(S)-alanyl}-2-carboxyperhydroindole.

1 g (4.17 m mols) of (2S)-1-[(S)-alanyl]-2-carboxyperhydroindole, prepared as described in Example 3, Step F, and 4.72 g (19 m mols) of ethyl [(1RS)-1-ethoxycarbonylethylthio]-pyruvate are dissolved in 50 ml of anhydrous ethanol in the presence of 15 g of molecular sieve 4 Å. After 45 minutes' stirring at room temperature, 0.25 g of sodium cyanoborohydride in solution in 2.25 ml of anhydrous ethanol are added within 6 hours.

After the molecular sieve has been separated off by filtration, the filtrate is concentrated to dryness under reduced pressure and the residue is dissolved in 100 ml of diethyl ether. The solution is extracted with 2×100 ml of distilled water, then dried over calcium sulphate, filtered and chromatographed over 200 g of silica (Merck F 254), washing out with a 180/20 methylene chloride/methanol mixture. 0.5 g (25%) of the desired product are obtained in the form of the sodium salt.

Analysis $C_{22}H_{35}N_2NaO_7S$:

|  | C % | H % | N % | S % |
|---|---|---|---|---|
| Calculated | 53.43 | 7.13 | 5.66 | 6.48 |
| Found | 53.28 | 7.09 | 5.19 | 5.92 |

The intermediate ethyl [(1RS)-1-ethoxycarbonylethylthio]-pyruvate is prepared by condensing ethyl bromopyruvate with (RS)-ethyl thiolactate in the presence of pyridine according to the process described for related derivatives in the J. of Heter. Chem. (1973) 10/4 p. 679–681).

b.p.$_{15}$=165–170; Yield 67%.

EXAMPLE 5

(2S)-1-[N-(2-ethoxycarbonylmethylthio-(1RS)-1-ethoxycarbonylethyl)-(S)-alanyl]-2-carboxyperhydroindole.

Prepared as in Example 4, starting from 1 g (4.17 m mols) of (2S)-1-[(S)-alanyl]-2-carboxyperhydroindole, 4.45 g (1.9 mols) of ethyl ethoxycarbonylmethylthiopyruvate and 0.25 g of sodium cyanoborohydride.

After purification by chromatography, 0.26 g (14%) of the desired product are obtained.

Analysis $C_{21}H_{34}N_2O_7S$:

|  | C % | H % | N % | S % |
|---|---|---|---|---|
| Calculated | 55.00 | 7.47 | 6.11 | 6.99 |
| Found | 54.71 | 7.32 | 5.94 | 7.01 |

The intermediate ethyl ethoxycarbonylmethylthiopyruvate is prepared by condensing ethyl bromopyruvate with ethyl thioglycolate according to the process described by the reference quoted in Example 4.

b.p.$_{15}$=165–175 Yield 50%.

EXAMPLE 6

(2S)-1-{N-[3-(N-benzyloxycarbonyl-N-dicyclopropylmethylamino)-(1RS)-1-ethoxycarbonylpropyl]-(S)-alanyl}-2-carboxyperhydroindole.

Prepared as in Example 4, starting from 0.6 g of (2S)-1-[(S)-alanyl]-2-carboxyperhydroindole, 4.3 g of ethyl 4-[N-(benzyloxycarbonyl)-dicyclopropylamino]-2-oxobutyrate and 0.15 g of sodium cyanoborohydride.

After purification by chromatography, 1 g (67%) of the desired product is obtained.

Analysis $C_{33}H_{47}N_3O_7$:

|  | C % | H % | N % |
|---|---|---|---|
| Calculated | 66.31 | 7.93 | 7.03 |
| Found | 66.11 | 7.83 | 7.22 |

The intermediate ethyl 4-[N-(benzyloxycarbonyl)-dicyclopropylamino]-2-oxobutyrate is prepared in 6 stages in the following manner:

Stage 1: condensation of bromoacetaldehyde diethylacetal with ethyl 2-dithianylcarboxylate according to E. D. ELIEL, J. Org. Chem. (1972) vol. 37 2 p. 505–506.

Yield: 57% b.p.$_{0.07}$=130°–135° C.

Stage 2: the 2-(2,2-diethoxy-1-ethyl)-2-ethoxycarbonyl-1,3-dithiane obtained is converted into a semicarbazone of 2-(2-oxo-1-ethyl)-2-ethoxycarbonyl-1,3-dithiane by stirring with a solution of semicarbazide hydrochloride in water at room temperature for 24 hours. The semicarbazone, obtained in a yield of 88%, has a melting point (Kofler) of 183° C.

Stage 3: the above semicarbazone is converted into the corresponding aldehyde by stirring with pyruvic acid in an aqueous acetic acid solution according to R. E. BEYLER et al. (J. Ann. Chem. Soc. (1960) 82 p. 175). b.p.$_{0.8}$=140°–145° C. Yield: 50%.

Stage 4: the above-mentioned aldehyde is condensed with dicyclopropylmethylamine and the imine obtained is subjected to reduction according to the process described by J. W. LOWN and S. ITOH (Can. J. Chem. (1975) 53 p. 960), providing 2-[2-(dicyclopropylmethylamino)-ethyl]-2-ethoxycarbonyl-1,3-dithiane in a yield of 65%. Its hydrochloride melts at 150° (K.).

Stage 5: the derivative obtained in the previous stage is subjected to the action of benzyl chloroformate according to the process described in "Chemistry of the amino acids" vol. 2 p. 895 by GREENSTEIN and WINITZ (Wiley Editor). 2-{2-[N-(benzylcarbonyl)-dicyclopropylmethylamino]-1-ethyl}-2-ethoxycarbonyl-1,3-dithiane is a viscous oil, obtained in a yield of 93%.

Stage 6: By the action of N-bromosuccinimide in an aqueous acetone solution, the derivative obtained in the previous step is converted into ethyl 4-[N-(benzyloxycarbonyl)-dicylopropylamino]-2-oxobutyrate in a yield of 70%, according to the process described by E. J. COREY (J. Org. Chem. (1971) 36, 3553–60).

The compounds prepared in the preceding Examples, and also other compounds of formula (I) prepared in a similar manner, have been collated in the Table which follows. For the sake of convenience, the symbols A and n are only mentioned for the values where A=a benzene ring and n=1. For all the other compounds A means a saturated ring and n=0 (perhydroindole of formula I').

The Table gives the characteristic values of the compounds with regard to infra-red (IR) and nuclear magnetic resonance (NMR):

s is for singlet,
d is for doublet,
q is for quadruplet,
m is for multiplet.

TABLE

| Compound No. | q | R₁ | R₂ | R₃ | FORM (salt) | I.R. (νₛ in cm⁻¹) | NMR in CDCl₃: chemical shifts (ppm)/TMS |
|---|---|---|---|---|---|---|---|
| 1 (Ex. 1) (A benzene n = 1) | 0 | $CH_3$ | H | $CH_3$ | ammonium salt | NH: 3500–2300 C=O: 1600 | m.: 4H(7,4)  d.: 2H(5,3) s.: 2H(4,8) 3H(5,3–4,1)  6H(1,8) |
| 2 (Ex. 2) (A benzene n = 1) | 1 | $CH_3$ | H | $CH_3$ | ammonium salt | — | Peaks: 5H(3,5–3) 4H(3,3) q.: 1H(4–3,5) d.: 3H(1,45) 3H(1,2)  3H(4,7) |
| 3 (Ex. 3) | 0 | $CH_3$ | H | $CH_3$ | ammonium salt | NH: 3500–2300 C=O: 1600 | m.: 3H(4,8–4) Massifs:18H(2,5–1,3) |
| 4 | 0 | $CH_3$ | $C_2H_5$ | —CH₂CH₂—C₆H₅ | acid maleate | — | Peaks: 6H(4,6–3,7) 2H(2,5–3) s.: 5H(7,3) 19H(2,5–1)  2H(6,35) |
| 5 | 0 | $CH_3$ | $C_2H_5$ | —CH₂—S—CH(cyclopropyl)₂ | — | — | Peaks: 17H(1,6–0,8) 6H(4,5–3,5) 2H(5,7–5,2) 10H(0,7–0,1) 3H(3,2–1,9) |
| 6 | 0 | $CH_3$ | $C_2H_5$ | —CH₂—CH₂—CH(cyclopropyl)₂ | acid maleate | — | Peaks: 21H(2,7–1)  6H(4,6–3,7) s.: 2H(6,4) 11H(0,8–0,1) 4H(11,2) |
| 7 | 0 | $CH_3$ | $C_2H_5$  $CH_3$ | —CH₂—S—CH(cyclohexyl)₂ | acid maleate | — | Peaks: 20H(2,7–1,1) 4H(10,3) s.: 2H(6,4) 6H(4,7–3,9) |
| 8 | 0 | $CH_3$ | $C_2H_5$ | —CH₂—S—CH(cyclohexyl)₂ | sodium salt | NH 3700–3200 CO ester 1730 CO amide 1650–1600 | Peaks: 8H(4,7–3,2) d.: 2H(2,9) 39H(2,5–1) |
| 9 (Ex. 6) | 0 | $CH_3$ | $C_2H_5$ | —CH₂—CH₂—N—CH(COOCH₂—C₆H₅)₂, $CH_3$ | — | NH 3500–2300 CO ester 1730–1690 CO amide 1650–1600 | Peaks: 39H(4,6–0,15) s.: 2H(5,1) 5H(7,3) |
| 10 (Ex. 4) | 0 | $CH_3$ | $C_2H_5$ | (PS) —CH₂—S—CH—COOC₂H₅, $CH_3$ | sodium salt | NH 3300 CO ester 1725 CO amide 1620 | Peaks: 11H(4,5–2,6) s.: 2H(6,5) 4H exchangeable (11,1) 23H(2,5–1) |
| 11 | 0 | $CH_3$ | $C_2H_5$ | (S) —CH₂—S—CH—COOC₂H₅, $CH_3$ | acid maleate | — | Peaks: 9H(4,7–3,2) 25H(2,5–1) |
| 12 | 0 | $CH_3$ | $C_2H_5$ | —CH₂—CH₂—CH(CH₃)₂ | sodium salt | NH 3600–2300 CO ester 1725 CO amide 1630 | Peaks: 6H(3–4,5)   d.: 6H(1) 20H(1,2–2,5) |

TABLE-continued

| Compound No. | q | $R_1$ | $R_2$ | $R_3$ | FORM (salt) | I.R. ($v_s$ in cm$^{-1}$) | R.M.N. in CDCl$_3$; chemical shifts (ppm)/TMS |
|---|---|---|---|---|---|---|---|
| 13 | 0 | CH$_3$ | C$_2$H$_5$ | —CH$_2$—CH$_2$—NH—CH(—⌬)$_2$ | acetate | NH$_2^+$ 3600–2300 CO ester 1730 CO amide 1650–1550 | Peaks: 6H(4,5–3,3) q.: 2H 4H exchangeable (8,7–7,7) 35H(0,3–2,5) |
| 14 (Ex. 5) | 0 | CH$_3$ | C$_2$H$_5$ | —CH$_2$—S—CH$_2$—COOC$_2$H$_5$ | — | NH 3700–2500 C=O ester 1720 C=O amide 1625 | Peaks: 18H(2–1) 2H(2,5–2) q.: 4H(4,25) s.: 2H(3,4) 4H(4,5–3,2) d.: 2H(3) 2H exchangeable |
| 15 | 0 | CH$_3$ | H | —CH$_2$CH$_2$—NH—CH(—⌬)$_2$ | sodium salt, CH$_3$COONa | NH 3500–3000 C=O 1680–1550 | Peaks: 19H(2,5–0,9) 7H(4,5–2,5) s.: 3H(1,9) 8H(0,9–0,1) NMR in D$_2$O |
| 16 | 0 | CH$_3$ | C$_2$H$_5$ | n-C$_4$H$_9$ | sodium salt | NH 3600–3100 C=O ester 1725 C=O amide 1620 | Peaks: 6H(3–4,5) 27H(0,1–2,5) |
| 17 | 0 | CH$_3$ | C$_2$H$_5$ | n-C$_3$H$_7$ | — | NH 3300 C=O ester 1725 C=O amide 1620 | Peaks: 24H(2,4–0,7) s. 2H(6,8) 6H(4,6–3,4) |
| 18 | 0 | CH$_3$ | C$_2$H$_5$ | —CH$_2$—⌬ | sodium salt | NH 3300 C=O ester 1725 C=O amide 1610 | Peaks: 25H(2,5–0) 6H(4,5–3) |
| 19 | 0 | CH$_3$ | C$_2$H$_5$ | i-C$_3$H$_7$ | sodium salt | NH 3300 C=O ester 1725 C=O amide | Peaks: 5H(4,5–3) 25H(0,7–2,5) 1H(2,9) |
| 20 | 0 | CH$_3$ | C$_2$H$_5$ | C$_2$H$_5$ | sodium salt | NH 3600–2500 C=O ester 1730 C=O amide 1610 | Peaks: 6H(3–4,6) 23H(0,6–2,5) |
| 21 | 0 | CH$_3$ | C$_2$H$_5$ | —CH$_2$CH$_2$—N(COOC$_2$H$_5$)(S)—CH—CH$_3$ / COCH$_3$ | sodium salt | NH 3300 C=O ester 1735 C=O amide 1650–1600 | Peaks: 11H(4,6–2,9) s.: 3H(2,1) 26H(2,4–1) |
| 22 | 0 | CH$_3$ | C$_2$H$_5$ | n-C$_5$H$_{11}$ | sodium salt | NH 3300 C=O ester 1725 C=O amide 1610 | Peaks: 7H(3–5) 28H(0,5–2,6) |
| 23 | 0 | CH$_3$ | C$_2$H$_5$ | n-C$_6$H$_{13}$ | sodium salt | NH$_2^+$ 3600–3,47) C=O ester 1730 C=O amide 1650–1550 | Peaks: 6H(3–4,7) 2H exchangeable (5,9) 30H(0,8–2,6) |
| 24 | 0 | CH$_3$ | C$_2$H$_5$ | —CH$_2$CH$_2$—N—CH(—⌬)$_2$ | sodium salt | NH 3700 C=O ester 1730 C=O amide 1600 | Peaks: 32H(2,6–0) 10H(5–2,8) |
| 25 | 0 | CH$_3$ | C$_2$H$_5$ | n-C$_8$H$_{17}$ | trifluoroacetate | NH$_2^+$ 3500–2300 CO ester 1740 CO amide 1650 | Peaks: 6H(3,5–4,6) 3H exchangeable (8–9) 34H(0,6–2,7) |
| 26 (n = 1) | 0 | CH$_3$ | C$_2$H$_5$ | i-C$_4$H$_9$ | — | NH$_2^+$ 3340–3200–3400 CO ester 1720 CO amide 1650 | Peaks: 27H(2,2–0,7) 2H exchangeable (5,8) 7H(4,8–3) |
| 27 | 0 | —(CH$_2$)$_4$—NH$_2$ | C$_2$H$_5$ | n-C$_3$H$_7$ | bis-trifluoroacetate | NH$_2^+$ 3300–2300 CO acide 1780 C=O ester 1740 C=O amide 1650 | Peaks: 29H(2,5–0,7) 4H(4,5–3,5) 4H(2,5–3,5) RMN in D$_2$O |

Pharmacological study of the compounds of the invention.

The compounds according to the invention were tested by i.v. or p.o. administration to dogs during consciousness.

The blood pressure of the dogs was measured by means of a pressure detector (Statham P 23 Db) after catheterisation of the aorta through the femoral artery. The findings were recorded by means of a recording apparatus (Brush 400).

Angiotensin I and angiotensin II were injected into the animals intravenously at a dosage of 0.3 γ/kg. The compounds according to the invention were then administered orally or intravenously at a dosage of from 1 to 5 mg/kg.

It was observed that there was inhibition of the hypertensive effect of angiotensin I ranging from 50 to 100% which occurred 30 to 90 minutes after administration and which remained at from 40 to 80% more than 6 hours after administration. Certain compounds remained active after 24 hours, which is not the case with any compound known hitherto (particularly captopril, which is the only commercially available compound). In addition, the compounds of the invention seem to have no toxic effect ($LD_o > 500$ mg/kg i.p. in mice).

EXAMPLE OF FORMULATION (2S)-1-{N-[2-((1S)-1-ethoxycarbonylethylthio)-(1RS)-1-ethoxycarbonylethyl]-(S)-alanyl}-2-carboxyperhydroindole

|   |   |
|---|---|
| (maleate) | 10 mg |
| wheat starch | 120 mg |
| cornstarch | 115 mg |
| casein treated with formaldehyde | 20 mg |
| magnesium stearate | 15 mg |
| talc | 20 mg | for 1 tablet.

We claim:

1. A compound selected from the group consisting of iminodiacid compounds having the formula:

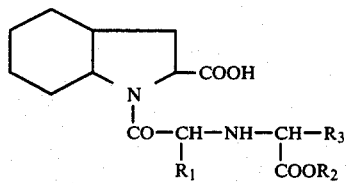

wherein
  $R_1$ represents lower-alkyl having 1 to 4 carbon atoms, inclusive,
  $R_2$ represents hydrogen or lower-alkyl having 1 to 4 carbon atoms, inclusive,
  $R_3$ is $-(CH_2)_3-CH_3$,
  in racemic form or as an optical isomer, a salt thereof with a pharmaceutically-acceptable inorganic or organic base, and an addition salt thereof with a pharmaceutically-acceptable inorganic or organic acid.

2. A compounds of to claim 1, the formula (I') in which $R_1$ is a methyl radical.

3. (2S)-1-{N-[(1RS)-1-ethoxycarbonylpentyl]-(S)-alanyl}-2-carboxyperhydroindole, its (S)-isomer or the sodium salt of these.

4. A pharmaceutical composition containing as active ingredient at least one compound according to claim 1, in conjunction with an inert, non-toxic pharmaceutically-acceptable compatible carrier or excipient.

5. A pharmaceutical composition containing as active ingredient a compound according to claim 3, in conjunction with an inert, non-toxic pharmaceutically-acceptable carrier or excipient.

6. A method for treating a patient suffering from hypertension, which comprises administering to said patient a therapeutically effective dose of a compound according to claim 1.

7. A method for treating a patient suffering from hypertension, which comprises administering to said patient a therapeutically-effective dose of a compound according to claim 3.

* * * * *

UNITED STATES PATENT AND TRADEMARK OFFICE
CERTIFICATE OF CORRECTION

PATENT NO. : 4,644,008

DATED : February 17, 1987

INVENTOR(S) : Michel Vincent, Georges Rémond and Michel Laubie

It is certified that error appears in the above-identified patent and that said Letters Patent is hereby corrected as shown below:

Title Page, [57] ABSTRACT, in the formula; "$R_1'$" should read -- $R'_1$ --

Col. 1, line 47; "N-N" should read -- N-Q --

Col. 3, line 25; "$R_1'$" should read -- $R'_1$ --

Col. 6, line 38; "dissoled" should read -- dissolved --

Col. 6, line 42; "monsodium" should read -- monosodium --

Col. 7, line 51; "$C_{17}H_{25}NHD\ 3O_5$" should read -- $C_{17}H_{25}N_3O_5$ --

Col. 7, line 64; "-carboxyinodline" should read -- -carboxyindoline --

Col. 7, line 67; "8" should read -- 18 --

Col. 8, line 25; "(DL)" should read -- (RS) --

Col. 12, line 38; "-(benzylcarbonyl)-" should read -- -(benzyloxycarbonyl)- --

Cols. 13&14, TABLE, column 5, compound # 10; "(PS)" should read -- (RS) --

Cols. 15&16, TABLE-continued, line 3; "R.M.N." should read -- NMR --

Cols. 15&16, TABLE-continued, compound # 27, Col. 7, first line;
  "CO acide" should read -- C=O acid --

Cols. 15&16, TABLE-continued, compound 27, last column, last line;
  "RMN" should read -- NMR --

Col. 18, line 22 (Cl. 2, li 1); "compounds of to claim" should read
  -- compound of claim --

Col. 18, line 30 (Cl. 4, li 4); delete "compatible"

Signed and Sealed this

Twentieth Day of September, 1988

Attest:

DONALD J. QUIGG

Attesting Officer

Commissioner of Patents and Trademarks